United States Patent
Ambrose et al.

(10) Patent No.: US 9,345,717 B2
(45) Date of Patent: May 24, 2016

(54) METHOD FOR IMPROVING DRUG TREATMENTS IN MAMMALS

(71) Applicant: Zavante Therapeutics, Inc., San Diego, CA (US)

(72) Inventors: Paul G. Ambrose, Latham, NY (US); Evelyn Ellis-Grosse, Marietta, GA (US)

(73) Assignee: Zavante Therapeutics, Inc., San Diego, CA (US)

( * ) Notice: Subject to any disclaimer, the term of this patent is extended or adjusted under 35 U.S.C. 154(b) by 32 days.

(21) Appl. No.: 14/497,022

(22) Filed: Sep. 25, 2014

(65) Prior Publication Data

US 2015/0148315 A1    May 28, 2015

Related U.S. Application Data

(60) Provisional application No. 61/882,436, filed on Sep. 25, 2013.

(51) Int. Cl.
*A61K 31/665* (2006.01)
*C12Q 1/18* (2006.01)

(52) U.S. Cl.
CPC ............... *A61K 31/665* (2013.01); *C12Q 1/18* (2013.01)

(58) Field of Classification Search
CPC ............................. A61K 31/665; C12Q 1/18
See application file for complete search history.

(56) References Cited

FOREIGN PATENT DOCUMENTS

WO        2011008193        1/2011

OTHER PUBLICATIONS

Drugs.com. "Fosfomycin." © Jun. 3, 2015. Available from: < http://www.drugs.com/cdi/fosfomycin.html >.*

Ambrose PG, Bhavnani SM, Rubino CM, Louie A, Gumbo T, Forrest A, Drusano GL. Pharmacokinetics—pharmacodynamics of antimicrobial therapy: It's not just for mice anymore. Clin Infect Dis 2007; 44:79-86.
Craig WA, Ebert SC. Killing and regrowth of bacteria in vitro: a review. Scand J Infect Dis Suppl 1990; 74:63-70.
Falagas ME, Makris GC, Dimopoulos, G, Matthaiou DK. Heteroresistance: a concern of increasing clinical significance? Clin Microb Infection. 2008; 14(2):101-104.
Traunmüller F, Popovic M, Konz KH, Vavken P, Leithner A, Joukhadar C. A reappraisal of current dosing strategies for intravenous fosfomycin in children and neonates. Clin Pharmacokinet. 2011; 50:493-503.
Joukhadar C, Klein N, Dittrich P, Zeitlinger M, Geppert A, Skhirtladze K, Fossard M, Heinz G, Müller M. Target site penetration of fosfomycin in critically ill patients. J Antimicrob Chemother. 2003; 51:1427-1252.
Roussos N, Karageorgopoulos DE, Samonis G, Falagas ME. Clinical significance of the pharmacokinetic and pharmacodynamic characteristics of fosfomycin for the treatment of patients with systemic infections. Int J Antimicrob Agents. 2009; 34:506-515.

* cited by examiner

*Primary Examiner* — Noble Jarrell
*Assistant Examiner* — John S Kenyon
(74) *Attorney, Agent, or Firm* — Lewis Kohn & Walker LLP; David M. Kohn; Kari Moyer-Henry

(57) ABSTRACT

An improved method for identifying the size, shape and duration of drug exposure necessary to improve drug treatment in a subject with a bacterial infection. In addition, an improved method for identification of new dosing strategies which optimize the probability of positive treatment outcomes in subjects using resistance inhibitory concentration (RIC), wherein the subject has a bacterial infection caused by a bacterium with a propensity for heteroresistance. Further, an improved method for decreasing the potential for on-therapy drug resistance by determining a patient's RIC prior to administration of fosfomycin treatment, wherein RIC is utilized to differentiate the parameter which is best related to the driver or index of fosfomycin efficacy for the resistant subpopulation present and the required inhibitory concentration of those mutants.

19 Claims, 5 Drawing Sheets

METHOD FOR IMPROVING DRUG TREATMENTS IN MAMMALS

CROSS REFERENCE TO RELATED APPLICATIONS

This application is non-provisional patent application claiming the benefit of priority from Provisional Application Ser. No. 61/882,436, filed Sep. 25, 2013, the contents of which are incorporated by reference herein.

FIELD OF THE INVENTION

The present invention provides a method for identification of new dosing strategies which optimize the probability of positive treatment outcomes in mammals. Specifically, the present invention provides a method of novel dosing regimens for treatment and prevention of the hetero-resistant subpopulation of gram-negative bacteria using fosfomycin.

BACKGROUND OF THE INVENTION

Antimicrobial agents can be characterized based upon the pharmacokinetic-pharmacodynamic (PK-PD) measure most predictive of efficacy.[i] For antimicrobial agents, the three most common PK-PD measures are the percentage of time during the dosing interval that drug concentration remains above the MIC (% T>MIC), the ratio of the area under the concentration-time at 24 hours to the MIC ($AUC_{0-24}$:MIC ratio) and the ratio of the maximal drug concentration to the MIC ($C_{max}$:MIC). Preliminary identification of the PK-PD measure most closely associated with efficacy of an agent can be made by examining the agent's pattern of bactericidal activity in a dynamic infection model or by its pattern of bactericidal activity in a static in vitro test system in combination with knowledge of the presence and duration of post-antibiotic effects.

Some agents, such as tobramycin and ciprofloxacin, display a concentration-dependent pattern of bactericidal activity over a broad range of drug concentrations.[ii] That is, as drug concentration increases, so too does the rate and extent of bactericidal activity. On the other hand, other agents such as the β-lactam class agents display a time-dependent pattern of bactericidal activity.[ii] For these agents, concentration-dependent bacterial killing occurs over a narrow range of drug concentrations.

It is likely that prolonged exposure to antimicrobial agents exerts increased pressure for selection of microbial subpopulations that are resistant to the therapy administered.[iii] According to the mutant selection window hypothesis, there is an antibiotic concentration above the MIC (termed the mutation prevention concentration) at which selective amplification of single-step, drug-resistant mutants may occur. Such mutants proliferate readily in the absence of competition with the inhibited susceptible cells of the wild-type strain, thereby giving rise to a new resistant population with a higher MIC than that for the wild-type strain. This observation has implications for patients with infections at sites where the penetration of antibiotics is suboptimal, despite the appropriate dosage scheme, e.g. abscesses and endocardial vegetations.

Heteroresistance may be the precursor stage leading to the emergence of a resistant bacterial strain. Recent prevalence in the occurrence of heteroresistant *Staphyloccocus aureus* resulting in increases in treatment failure and mortality have renewed the urgency for development of methods for the rapid laboratory detection of heteroresistant strains. In order to prevent the spread and/or emergence of heteroresistant strains, antibiotics should be administered with prudence. Shorter antimicrobial regimens that are able to achieve the maximum effectiveness with the minimum selective pressure are necessary. There remains a need in the art for methods of identifying initial dose, maintenance dose and dose frequency necessary to achieve maximum treatment effectiveness with minimal selective pressure.

In light of the above, it is an object of the present invention to provide the desired features described herein as well as additional advantages such as decreasing the potential for on-therapy drug resistance and the spreading and/or emergence of heteroresistant bacterial strains.

BRIEF DESCRIPTION OF THE DRAWINGS

The novel features of this invention, as well as the invention itself, both as to its structure and its operation, will be best understood from the accompanying drawings, taken in conjunction with the accompanying description, and in which.

DETAILED DESCRIPTION OF THE INVENTION

Figure 1:
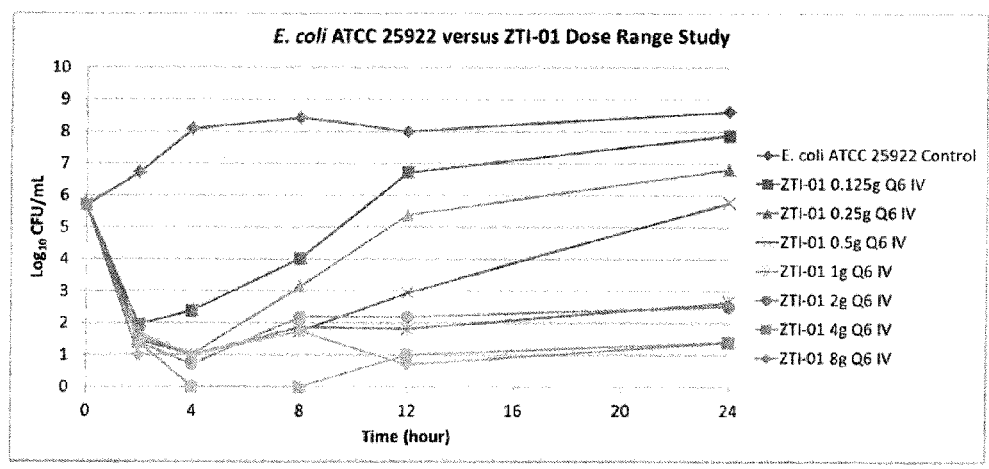
FIG. 1 illustrates the bactericidal effect of varying fosfomycin exposures as measured by dose on a wild-type strain of *Escherichia coli*.

Definitions:

MIC as used herein refers to the minimum inhibitory concentration (MIC) of an antimicrobial that will inhibit the visible growth of a microorganism after overnight incubation. MICs are important in diagnostic laboratories to confirm resistance of microorganisms to an antimicrobial agent and also to monitor the activity of new antimicrobial agents. A MIC is generally regarded as the most basic laboratory measurement of the activity of an antimicrobial agent against an organism. Clinically, the MICs are used not only to determine the amount of antibiotic that a patient will receive but also the type of antibiotic used, which in turn lowers the opportunity for microbial resistance to specific antimicrobial agents. Applying MIC testing to a number of bacterial strains in the same species provides an estimate of the concentration that inhibits 50% ($MIC_{50}$) and 90% ($MIC_{90}$) of bacterial isolates and can indicate shifts in susceptibility of bacterial populations to antibiotics.

RIC as used herein refers to the resistant inhibitory concentration and identifies the concentrations of antimicrobial required to inhibit the less susceptible or 'resistant' mutant subpopulation of organisms. RIC is a new term coined by the inventors of the present invention and is utilized throughout the specification herewith.

Pharmacokinetics (PK) as used herein refers to the time course of drug concentrations in plasma (and sometimes in other fluids and tissues) resulting from a particular dosing regimen.

Pharmacodynamics (PD) as used herein expresses the relationship between drug concentrations in plasma (and sometimes in other fluids and tissues) and a resulting pharmacological effect.

A PK/PD Model combines: 1) A model describing drug concentrations vs. time (PK) with 2) A model describing the relationship of effect vs. concentration (PD), and 3) A statistical model describing variation in intra- and inter-individual PK/PD models to predict the time-course and variability of effect vs. of time.

Fosfomycin is a broad-spectrum antibiotic with broad antibacterial activity against both Gram-positive and Gram-negative pathogens, with useful activity against *E. faecalis, E. coli*, and various Gram-negatives like *Citrobacter* and *Proteus*.

Dose-fractionation and dose-ranging studies in a pre-clinical model system will discriminate the pharmacologic determinant of drug efficacy and thereby improve drug treatment in mammals. Moreover such studies will identify the size, shape and duration of drug exposure necessary to improve drug treatment in mammals.

Bacterial infection as used herein refers to an infection caused by bacteria selected from the group consisting of *Acinetobacter* spp., *Campylobacter* spp., *Citrobacter* spp., *Enterobacter* spp, *Escherichia coli, Haemophilus influenza, Klebsiella oxytoca, Klebsiella pneumonia, Neisseria meningitides, Neisseria gonorrhea, Pseudomonas aeruginosa, Proteus mirabilis, Proteus vulgaris, Providencia rettgeri, Salmonella* spp., *Serratia marcessans, Shigella* spp., and *Yersinia enterocolitica*.

Heteroresistance as used herein refers to mixed populations of drug-resistant and drug-sensitive cells in a single clinical specimen or isolate where the proportion of resistant organisms may not be explicable by the natural "background" mutation rate alone; and even more precisely, heteroresistance can be defined as resistance to certain antibiotics expressed by a subset of a microbial population that is generally considered to be susceptible to these antibiotics according to traditional in-vitro susceptibility testing.

Dose and dosage and related terms as used herein refer to the units that contain a predetermined quantity of the active ingredient calculated to produce a desired therapeutic effect. One of skill in the art will understand that the term "maintenance dose" can refer to a single dose as well as more than one dose. The maintenance dose is the total amount of active ingredient administered during the maintenance dose phase of treatment.

Previous studies has suggested fosfomycin % Time>MIC as the PK-PD measure most closely associated with efficacy.[iv, v, vi] Given the discordance between the dose-ranging studies described in FIG. 1, which do not suggest % Time>MIC as the PK-PD measure most closely associated with efficacy, and studies in the literature that suggest % Time>MIC is predictive of fosfomycin efficacy, additional studies were warranted.

EXAMPLE 1

Figure 2:
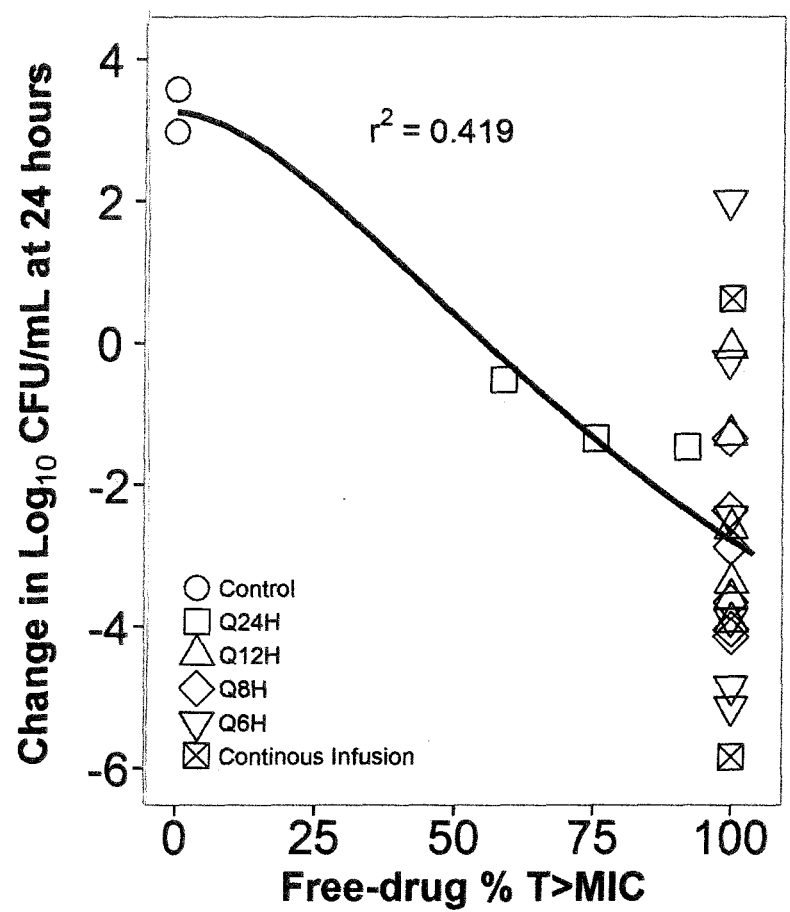
FIG. 2 illustrates the impact of fosfomycin dosing interval on the change in bacterial density at 24 hours.

A dose-fractionation study was conducted utilizing a wild-type strain of *Escherichia coli* (ATCC 25922; fosfomycin MIC=0.5 mg/L agar; 1 mg/L broth microtiter) in a one-compartment in vitro infection model where the human drug concentration-time profile was simulated over a 24 hour study period. FIG. 2 shows the study results, where each regimen was identical in terms of total daily dose and % T>MIC (100%) but the change in bacterial density at 24 hours varied dramatically over an 8 $\log_{10}$ range. These results provide evidence that % T>MIC is not the PK-PD measure that best describes fosfomycin efficacy.

One reason for failure of % Time>MIC to describe fosfomycin efficacy is the presence of an inherently fosfomycin-resistant *E. coli* subpopulation (agar MIC 32-64 mg/L) within the standard starting inoculum of the susceptibility test method ($5\times10^5$ CFU/mL). Another reason may be the volume of the micro-titer well (100-200 µL) used in the test method is small, containing 50,000-100,000 CFU. The inherently fosfomycin-resistant subpopulation has a frequency of 1 in 350,000 CFU. Thus, for fosfomycin, the standard susceptibility test method is an insensitive measure of the drug concentration required to inhibit a clinically relevant bacterial inoculum.

In such a circumstance, one way to overcome the poor sensitivity of the susceptibility test method is to increase the inoculum size and/or the volume of test system. The one-compartment in vitro infection model is a much more sensitive tool to measure the drug concentration required to inhibit a clinically relevant bacterial inoculum owing to its ability accommodate a higher inoculum and the larger volume (125 mL) of the test system. For this reason, dose-fractionation studies were conducted using a one-compartment in vitro infection model to identify the PK-PD measure most closely associated with efficacy.

EXAMPLE 2

Figure 3:
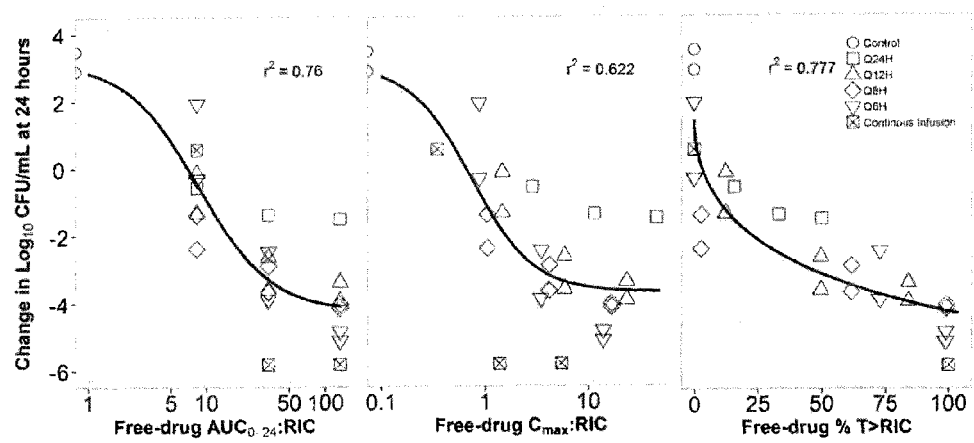
FIG. 3 illustrates the results of a dose-fractionation study evaluating the PK-PD relationship profile of fosfomycin against *Escherichia coli*.

FIG. 3 shows the results of a dose-fractionation study that evaluated the PK-PD profile of fosfomycin against *E. coli* (ATCC 25922; fosfomycin resistant subpopulation agar MIC=32 mg/L) in a one-compartment in vitro infection model where the human drug concentration-time profile was simulated over a 24 hour study period. Note the relatively stronger relationship between the change in bacterial density and $AUC_{0-24}$:RIC ratio and % T>RIC compared with that for $C_{max}$:RIC ratio, where RIC is the concentration needed to inhibit the fosfomycin-resistant subpopulation.

There are two important implications of these findings, one relates to how fosfomycin should be dosed clinically and the other relates to diagnostic testing. First, based upon the strength of the relationship between the change in bacterial density and $AUC_{0-24}$:RIC ratio and % T>$MIC_R$, it is tempting to conclude that either PK-PD measure could be used for dose optimization. However, further examination of these data reveals that neither PK-PD measure alone fully explains the relationship between change in bacterial density and drug exposure. Note that at maximally effective $AUC_{0-24}$:RIC ratios and free-drug % T>RIC, the magnitude of bacterial killing is related to the dosing interval. That is, as the duration of the dosing interval decreases, the amount of bacterial killing increases. Thus, one can conclude that the way any given drug exposure is delivered will impact bacterial killing. In other words, the shape of the $AUC_{0-24}$ is of critical importance with regard to bacterial killing. When one considers the rapidity and depth of bacterial kill within the first 2 hours of therapy (FIG. 1) and the relationship between bacterial killing and dosing interval (FIG. 3), the bactericidal activity of fosfomycin would likely benefit from alternative approaches, such as an initial-loading of the drug exposure. An initial-load dosing strategy is one that delivers larger drug exposures early (initial 24 to 48 hours) in therapy when the bacterial density and the risk of amplification of drug-resistant bacterial subpopulations is the greatest. Such studies are currently being planned.

Second, there is an opportunity to adjust technical details of the disc or a broth dilution test method to detect and quantitate the drug-resistant subpopulation. Such a test may provide a diagnostic tool that can be used to discriminate the relevant MIC to further identify a RIC, which thereby identifies patients likely to respond to fosfomycin therapy. One variable that should be considered is the duration of the susceptibility test study, which is standardly 18 to 24 hours. Extending the test duration may discriminate the presence and drug-susceptibility of a less-drug-susceptible population (RIC). Such studies are currently being planned.

EXAMPLE 3

In vivo animal studies utilizing the neutropenic murine-thigh model were conducted to confirm key results obtained from the in vitro PK-PD infection models. Initial goals of the studies were to confirm the presence of a clinically-relevant fosfomycin-resistant subpopulation in vivo and to confirm % T>RIC was the PK-PD measure that predicted response.
Methods In brief, six-week-old specific-pathogen-free female CD1 (ICR/Swiss) mice were rendered neutropenic by two intraperitoneal injections of cyclophosphamide, 150 mg/kg of body weight 4 days prior to the study and 100 mg/kg 1 day prior to the study. The challenge isolate was *Escherichia coli* ATCC 25922 (fosfomycin MIC, 1 mg/L), which was the same strain used in the aforementioned in vitro PK-PD infection model studies. Approximately $10^6$ CFU/mL of the challenge isolate at mid-log-phase growth were injected into both thighs 2 hours before beginning therapy. The number of organisms in the thigh at the start of therapy in the following studies varied from $7 \times 10^6$ to $2 \times 10^7$ colony forming units (CFU)/thigh. Groups of 2 mice per time point were treated with fosfomycin using multiple dosing regimens administered over 24 hours at dosing intervals of 3, 6, 12, and 24 hours. At 24 hours mice were sacrificed and homogenates of the posterior thigh muscle tissue were washed then cultured on drug-free and fosfomycin-containing (3 and 256 mg/L) plates. All drug-containing plates were supplemented with 25 mg/L of glucose-6-phosphate.

To determine which PK-PD measure best described efficacy, the number of bacteria in the thigh at the end of 24 hours of therapy (or earlier for some of the lowest doses) was correlated with 1) the $C_{max}$:MIC ratio, 2) the 24-hour $AUC_{0-24}$:MIC ratio, 3) the percentage of the dosing interval during that serum concentrations exceed the MIC, and 4) the percentage of the dosing interval during that serum concentrations exceed the RIC for each of the dosage regimens studied. The PK-PD index values for those doses not specifically studied were linearly extrapolated from the pharmacokinetic data. The correlation between efficacy and each of the three PK-PD indices was determined by nonlinear least-squares multivariate regression. The coefficient of determination ($R^2$) and visual data inspection were used to determine the PK-PD measure best associated with efficacy.

Figure 4:
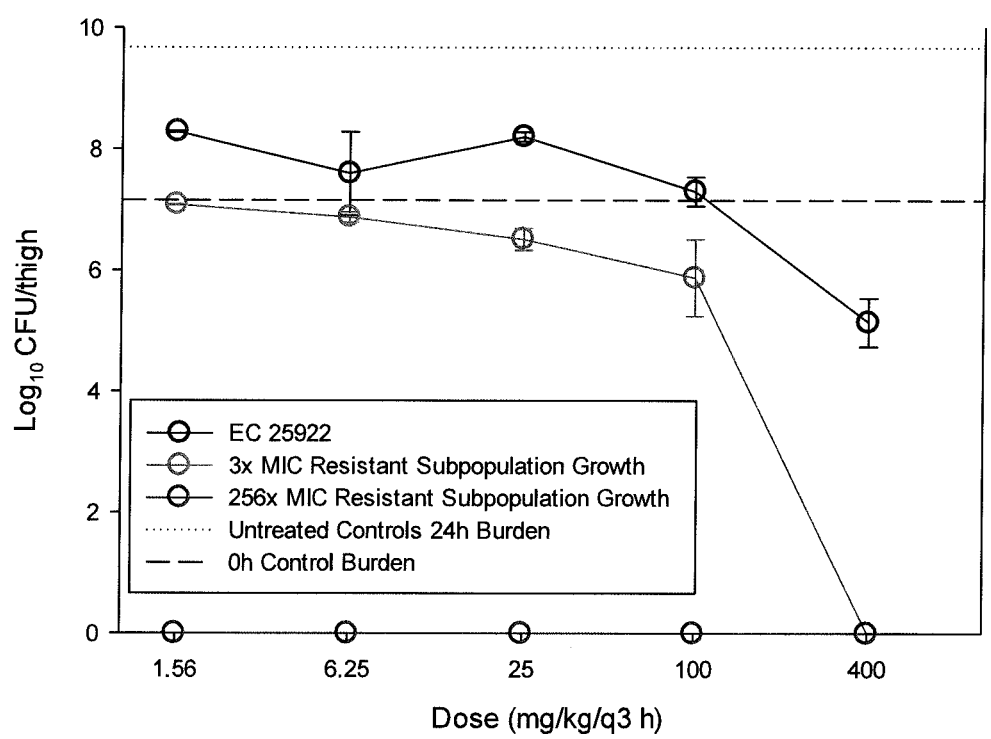
FIG. 4 illustrates bacterial density of the total bacterial population and the drug-resistant subpopulation in the thighs of neutropenic mice after 24 hours of therapy.

FIG. 4 shows the bacterial density of the total bacterial population and the drug-resistant subpopulation in the thighs of neutropenic mice after 24 hours of therapy for a dose range of 1.56 to 400 mg/kg administered every 3 hours. Note that as the fosfomycin dose increases the density of the drug-resistant subpopulation decreases and is eliminated at the highest dose-level. These studies demonstrate that the drug-resistant bacterial subpopulation identified in the in vitro PK-PD infection models is relevant in vivo and can be suppressed by increased fosfomycin exposure (dosing).

Figure 5:
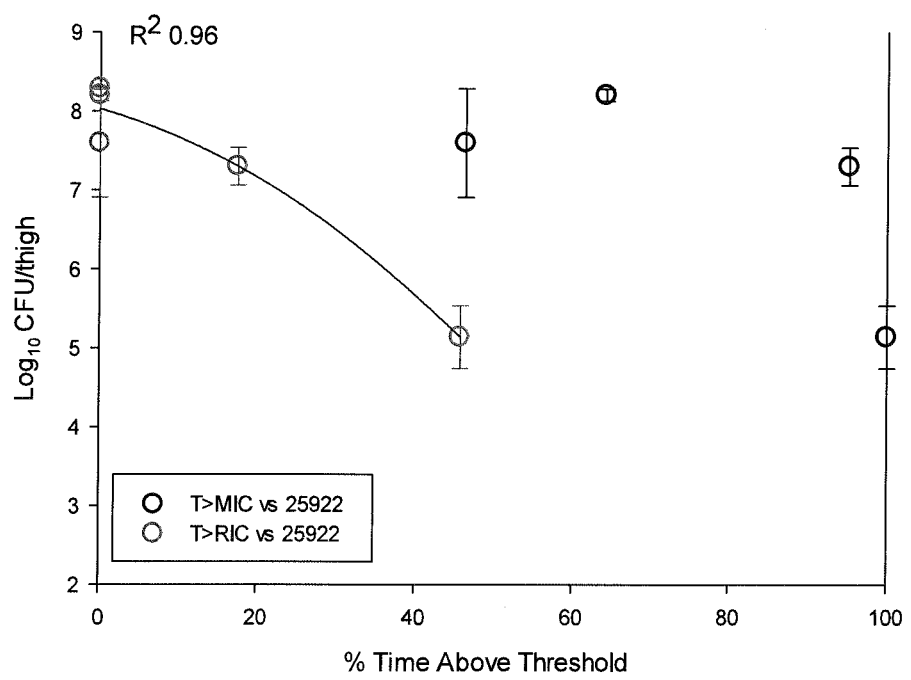
FIG. 5 illustrates the change in bacterial density indexed to % Time>MIC and % T>RIC in the thighs of neutropenic mice after 24 hours of therapy.

FIG. 5 shows the relationship between % T>Threshold, where the threshold is the nominal MIC or the MIC value of the resistant bacterial subpopulation (RIC), and change in $log_{10}$ CFU in the thighs of neutropenic mice after 24 hours of therapy. Note that % T>RIC was well-correlated with change in bacterial density over the dose-range studies, which % Time>MIC was non-informative.

The findings confirmed the results of the in vitro PK-PD infection models. Utilizing the neutropenic murine-thigh infection model, the presence of a clinically relevant fosfomycin-resistant subpopulation was confirmed. Further, the PK-PD parameter that best predicted in vivo response was confirmed to be % T>RIC.

One embodiment of the present invention provides a method for identification of new dosing strategies which optimize the probability of positive treatment outcomes in subjects using resistance inhibitory concentration (RIC), the method comprising:
  a) obtaining a sample from a subject suffering from a bacterial infection;
  b) identifying the presence of bacteria having a propensity for heteroresistance in said sample;
  c) determining the RIC of fosfomycin required to prevent heteroresistance of the bacteria identified in step b);
  d) utilizing the RIC determined in step c) to calculate optimum initial dose, maintenance dose and dose frequency to maximize the killing of bacteria present in said sample; and
  e) administering fosfomycin to a subject according to the optimum initial dose, maintenance dose and dose frequency identified in step d),
  wherein the bacterial density is effectively reduced and heteroresistance is prevented.

Another embodiment of the present invention provides a method for identifying the size, shape and duration of drug exposure necessary to improve drug treatment in mammals.

In still another embodiment of the present invention, the bacterial infection is caused by bacteria selected from the group consisting of *Acinetobacter* spp., (*Campylobacter* spp., *Citrobacter* spp., *Enterobacter* spp, *Escherichia coli*, *Haemophilus influenza*, *Klebsiella oxytoca*, *Klebsiella pneumonia*, *Neisseria meningitides*, *Neisseria gonorrhea*, *Pseudomonas aeruginosa*, *Proteus mirabilis*, *Proteus vulgaris*, *Providencia rettgeri*, *Salmonella* spp., *Serratia marcessans*, *Shigella* spp., and *Yersinia enterocolitica*.

In yet another embodiment of the present invention, fosfomycin may be administered to a subject in a dose ranging from 1.56 mg/kg to 3 g/kg. In a preferred embodiment, fosfomycin may be administered to a subject in a dose ranging from 2 mg/kg to 1 g/kg. In a most preferred embodiment, fosfomycin may be administered to a subject in a dose ranging from 2 mg/kg to 400 mg/kg.

In another embodiment of the present invention there is provided a method for decreasing the potential for on-therapy drug resistance by determining a patient's RIC prior to administration of fosfomycin treatment. In this embodiment, RIC is utilized to differentiate the parameter which is best related to the driver or index of fosfomycin efficacy for the resistant subpopulation present and the required inhibitory concentration of those mutants. In this embodiment, the method comprises:
  a) obtaining a sample from a subject suffering from a bacterial infection;
  b) identifying the presence of bacteria having a propensity for heteroresistance in said sample;
  c) determining the RIC of fosfomycin required to prevent heteroresistance of the bacteria identified in step b);

d) utilizing the RIC determined in step c) to calculate optimum initial dose, maintenance dose and dose frequency to maximize the killing of bacteria present in said sample; and e) administering fosfomycin to a subject according to the optimum initial dose, maintenance dose and dose frequency identified in step d), wherein the bacterial density is effectively reduced and heteroresistance is prevented.

In still another embodiment of the present invention there is provided a method for treating a subject with a bacterial infection, the method comprising:

a) obtaining a sample from a subject suffering from a bacterial infection;

b) identifying the presence of bacteria having a propensity for heteroresistance in said sample;

c) determining the RIC of fosfomycin required to prevent heteroresistance of the bacteria identified in step b);

d) utilizing the RIC determined in step c) to calculate optimum initial dose, maintenance dose and dose frequency to maximize the killing of bacteria present in said sample; and e) administering fosfomycin to a subject according to the optimum initial dose, maintenance dose and dose frequency identified in step d), wherein the bacterial density is effectively reduced and heteroresistance is prevented.

It will be appreciated that details of the foregoing embodiments, given for purposes of illustration, are not to be construed as limiting the scope of this invention. Although several embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

[i] Ambrose P G, Bhavnani S M, Rubino C M, Louie A, Gumbo T, Forrest A, Drusano G L. Pharmacokinetics-pharmacodynamics of antimicrobial therapy: It's not just for mice anymore. *Clin Infect Dis* 2007; 44:79-86.

[ii] Craig W A, Ebert S C. Killing and regrowth of bacteria in vitro: a review. *Scand J Infect Dis* Suppl 1990; 74:63-70.

[iii] Falagas M E, Makris G C, Dimopoulos, G, Matthaiou D K. Heteroresistance: a concern of increasing clinical significance? *Clin Microb Infection.* 2008; 14(2):101-104.

[iv] Traunmüller F, Popovic M, Konz K H, Vavken P, Leithner A, Joukhadar C. A reappraisal of current dosing strategies for intravenous fosfomycin in children and neonates. *Clin Pharmacokinet.* 2011; 50:493-503.

[v] Joukhadar C, Klein N, Dittrich P, Zeitlinger M, Geppert A, Skhirtladze K, Fossard M, Heinz G, Müller M. Target site penetration of fosfomycin in critically ill patients. *J Antimicrob Chemother.* 2003; 51:1427-1252.

[vi] Roussos N, Karageorgopoulos D E, Samonis G, Falagas M E. Clinical significance of the pharmacokinetic and pharmacodynamic characteristics of fosfomycin for the treatment of patients with systemic infections. *Int J Antimicrob Agents.* 2009; 34:506-515.

The invention claimed is:

1. A method of identifying the dosing regimen required to optimize the probability of positive treatment outcomes in a subject using resistance inhibitor concentration (RIC), the method comprising:

a) obtaining a sample from a subject suffering from a bacterial infection;

b) identifying the presence of bacteria in said sample;

c) determining the RIC of fosfomycin required to inhibit "resistant" mutant subpopulations of bacteria identified in step b);

d) utilizing the RIC determined in step c) to calculate optimum dosing interval over the first 24 hours to maximize the killing of bacteria present in said sample; and e) administering fosfomycin to a subject according to the optimum dosing interval determined in step d), wherein the bacterial density is effectively reduced and the fosfomycin-resistant subpopulation is inhibited.

2. The method of claim 1, wherein the bacterial infection is caused by bacteria selected from the group consisting of *Acinetobacter* spp., *Campylobacter* spp., *Citrobacter* spp., *Enterobacter* spp, *Enterococcus faecalis, Escherichia coli, Haemophilus influenza, Klebsiella oxytoca, Klebsiella pneumonia, Neisseria meningitides, Neisseria gonorrhea, Pseudomonas aeruginosa, Proteus mirabilis, Proteus vulgaris, Providencia rettgeri, Salmonella* spp., *Serratia marcessans, Shigella* spp., and *Yersinia enterocolitica.*

3. The method of claim 1, wherein the fosfomycin is administered to a subject in a dose ranging from 1.56 mg/kg to 400 mg/kg.

4. The method of claim 2, wherein the bacterial infection is an infection caused by *Escherichia coli.*

5. The method of claim 2, wherein the bacterial infection is an infection caused by *Enterococcus faecalis.*

6. The method of claim 1, wherein the subject is a mammal.

7. The method of claim 6, wherein the mammal is a human.

8. A method for decreasing on-therapy drug resistance using resistance inhibitor concentration (RIC), the method comprising:

a) obtaining a sample from a subject suffering from a bacterial infection;

b) identifying the presence of bacteria in said sample;

c) determining the RIC of fosfomycin required to inhibit "resistant" mutant subpopulations of bacteria identified in step b);

d) utilizing the RIC determined in step c) to calculate optimum dosing interval over the first 24 hours to maximize the killing of bacteria present in said sample; and e) administering fosfomycin to a subject according to the optimum dosing interval determined in step d), wherein the bacterial density is effectively reduced and the fosfomycin-resistant subpopulation is inhibited.

9. The method of claim 8, wherein the bacterial infection is caused by bacteria selected from the group consisting of *Acinetobacter* spp., *Campylobacter* spp., *Citrobacter* spp., *Enterobacter* spp, *Enterococcus faecalis, Escherichia coli, Haemophilus influenza, Klebsiella oxytoca, Klebsiella pneumonia, Neisseria meningitides, Neisseria gonorrhea, Pseudomonas aeruginosa, Proteus mirabilis, Proteus vulgaris, Providencia rettgeri, Salmonella* spp., *Serratia marcessans, Shigella* spp., and *Yersinia enterocolitica.*

10. The method of claim 8, wherein the fosfomycin is administered to a subject in a dose ranging from 1.56 mg/kg to 400 mg/kg.

11. The method of claim 9, wherein the bacterial infection is an infection caused by *Escherichia coli.*

12. The method of claim 9, wherein the bacterial infection is an infection caused by *Enterococcus faecalis*.

13. The method of claim 8, wherein the subject is a mammal.

14. The method of claim 13, wherein the mammal is a human.

15. A method for treating a subject with a bacterial infection using resistance inhibitor concentration (RIC), the method comprising:
   a) obtaining a sample from a subject suffering from a bacterial infection;
   b) identifying the presence of bacteria in said sample;
   c) determining the RIC of fosfomycin required to inhibit "resistant" mutant subpopulations of bacteria identified in step b);
   d) utilizing the RIC determined in step c) to calculate optimum dosing interval over the first 24 hours to maximize the killing of bacteria present in said sample; and
   e) administering fosfomycin to a subject according to the optimum dosing interval determined in step d), wherein the bacterial density is effectively reduced and the fosfomycin-resistant subpopulation is inhibited.

16. The method of claim 15, wherein the bacterial infection is caused by bacteria selected from the group consisting of *Acinetobacter* spp., *Campylobacter* spp., *Citrobacter* spp., *Enterobacter* spp, *Enterococcus faecalis, Escherichia coli, Haemophilus influenza, Klebsiella oxytoca, Klebsiella pneumonia, Neisseria meningitides, Neisseria gonorrhea, Pseudomonas aeruginosa, Proteus mirabilis, Proteus vulgaris, Providencia rettgeri, Salmonella* spp., *Serratia marcessans, Shigella* spp., and *Yersinia enterocolitica*.

17. The method of claim 15, wherein the fosfomycin is administered to a subject in a dose ranging from 1.56 mg/kg to 400 mg/kg.

18. The method of claim 15, wherein the subject is a mammal.

19. The method of claim 18, wherein the mammal is a human.

* * * * *